US005334732A

United States Patent [19]
Murray et al.

[11] Patent Number: 5,334,732
[45] Date of Patent: Aug. 2, 1994

[54] OXIDATION OF CEPHALOMANNINE WITH OZONE IN THE PRESENCE OF TAXOL

[75] Inventors: Christopher K. Murray; Timothy D. Ziebarth; Jeffrey T. Beckvermit, all of Boulder, Colo.

[73] Assignee: Hauser Chemical Research, Inc., Boulder, Colo.

[21] Appl. No.: 120,170

[22] Filed: Sep. 10, 1993

Related U.S. Application Data

[63] Continuation-in-part of Ser. No. 909,080, Jul. 2, 1992, abandoned.

[51] Int. Cl.[5] .................. C07D 305/00; C07D 407/00; C02F 1/70

[52] U.S. Cl. .................................... 549/510; 549/200; 435/123; 210/760

[58] Field of Search ................ 435/123; 549/200, 510; 210/760

[56] References Cited

PUBLICATIONS

Streitweser et al. *Intro. to Organic Chemistry,* 3d Edition, MacMillan Publishing, New York, pp. 266 & 366.

Kingston et al. *Journal of Natural Products,* vol. 55(2) pp. 259-261, 1992.

Bunnella, "Preparation, Properties, and Reactions of Carbonyl Oxides", Chem. Rev. 1991, 335-362.

Odinokov et al., "Ozonolysis—A Modern Method in the Chemistry of Olefins", Russian Chemical Reviews, 50 (7), 1981.

Veysoglu et al., "A Convenient Method for the Control of Selective Ozonizations of Olefins", Synthesis, Oct. 1980.

Greenwood et al., "Studies in Ozonolysis. II Quantitatives Study of the Ozonation of 3-Octene", J. Org. Chem. pp. 1551-1554.

Criegee, "Mechanism of Ozonolysis", Chem. Internat. Edit, vol. 14, No. 11 (1975).

Yamamoto et al., "Ozonation of Organic Compounds. 4. Ozonolysis of a,b-unsaturated Carbonyl Compounds in Protic Solvents", J. Org. Chem., 1981, 46, 250-254.

Magri et al., "Modified Taxole. 2. Oxidation Products of Taxol", J. Org. Chem. 1986, 51, 797-802.

Kingston et al., "Modified Taxols. 7. A Method For The Separation of Taxol and Cephalomannine", J. of Natural Products, vol. 55, No. 2, pp. 259-261 (1992).

*Primary Examiner*—David M. Naff
*Assistant Examiner*—L. Blaine Lankford
*Attorney, Agent, or Firm*—Dean P. Edmundson

[57] ABSTRACT

A process for oxidizing cephalomannine and related taxanes in the presence of taxol is described. The process involves the use of ozone which is able to oxidize cephalomannine and easily oxidizable taxanes while leaving taxol essentially unchanged. Taxol can then be separated from the oxidized cephalomannine and other oxidized taxanes using conventional procedures. A process for oxidizing taxanes is also provided.

5 Claims, 6 Drawing Sheets

Comparison of Chemical Oxidation by Ozone and Osmium Tetroxide

Figure 6

OXIDATION OF CEPHALOMANNINE WITH OZONE IN THE PRESENCE OF TAXOL

CROSS-REFERENCE TO RELATED APPLICATION

This application is a continuation-in-part of our co-pending application Ser. No. 07/909,080, filed Jul. 2, 1992, now abandoned.

FIELD OF THE INVENTION

This invention relates to oxidation of cephalomannine and other oxidizable taxanes in extracts of biomass containing a complex mixture of compounds. More particularly, this invention relates to oxidation of cephalomannine in the presence of taxol to simplify the isolation and purification of taxol.

BACKGROUND OF THE INVENTION

Figure 1:
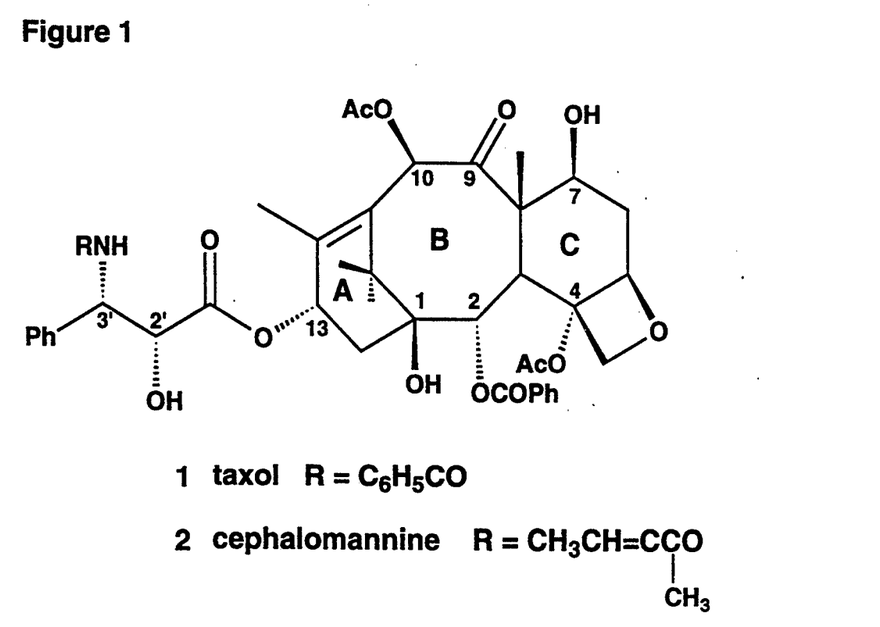
FIG. 1 compares the structure of taxol and cephalomannine.

Extracts of taxus species and cell cultures of taxus contain taxol, a promising chemotherapeutic agent which was recently approved by the Food and Drug Administration for the treatment of refractory ovarian cancer. Currently, taxol is isolated on a large scale from the bark of *taxus brevifolia*. However, taxol can be potentially isolated from other parts of taxus and also from cell culture of taxus. The isolation of taxol from any natural source is complex. A particularly difficult and expensive part of the isolation of taxol is the separation of a closely-related diterpenoid compound called cephalomannine. The structures and chemical properties of taxol and cephalomannine are similar. The only structural difference between the two compounds involves the tail portion of the molecule (see 1 and 2 in FIG. 1). Separation of taxol from cephalomannine is very difficult, but it can be done by means of chromatography. This is an expensive method when performed on a large commercial scale.

Figure 2:
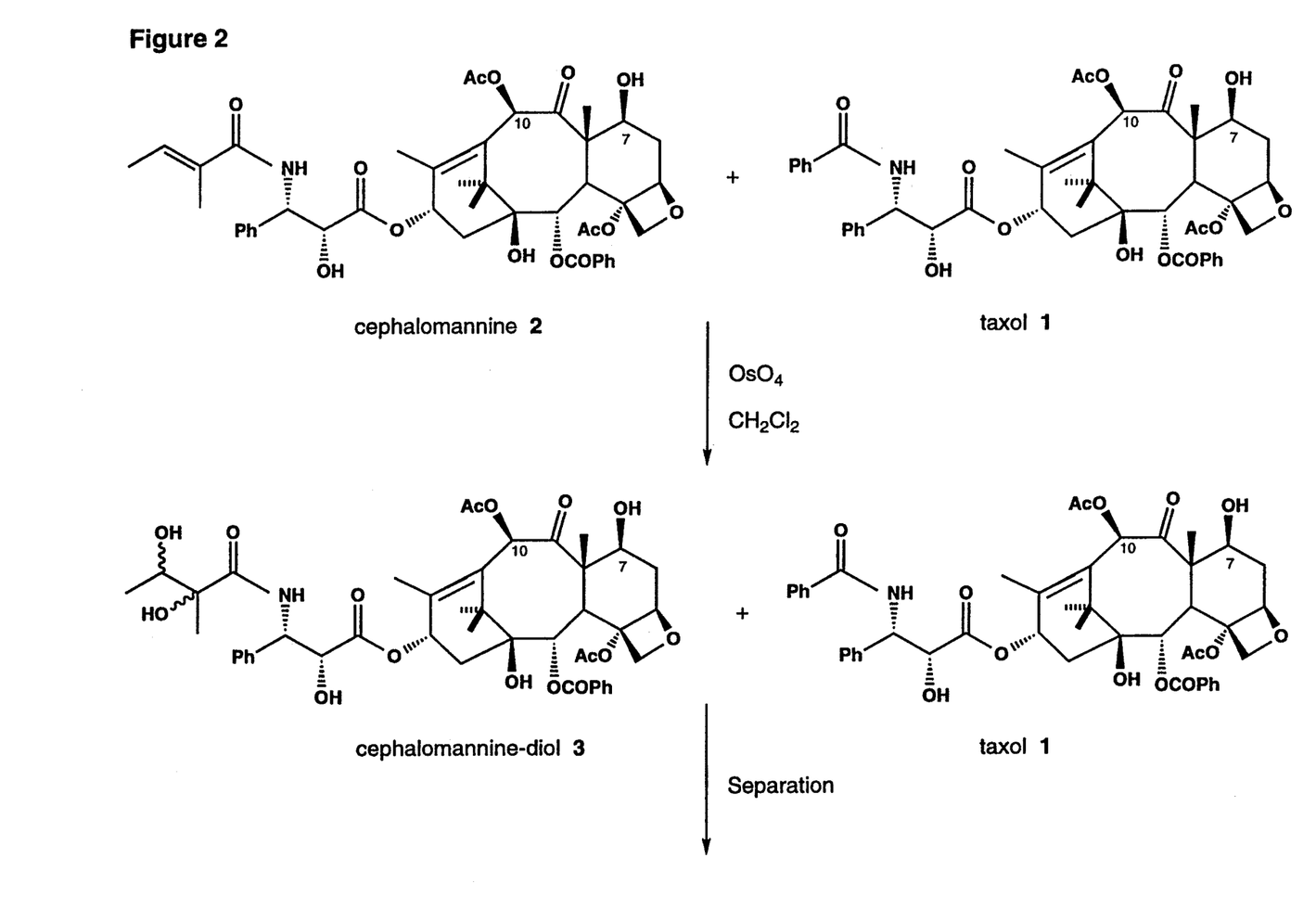
FIG. 2 shows the reaction of cephalomannine with osmium tetroxide.

Chemical modifications of the tail portion of cephalomannine in the presence of taxol in purified and partially-purified taxane mixtures has been described by Kingston, Journal of Natural Products, Vol. 55, No. 2, pp. 259-261, February, 1992, incorporated herein by reference. In the partially-purified mixture the taxol and the cephalomannine were present in an amount of about 80% by weight. Selective oxidation of the riglate group of cephalomannine using osmium tetroxide under stoichiometric or catalytic conditions (Kingston's method) yielded a diol (compound 3). The diol was separated from the reaction mixture by chromatography. This is shown in FIG. 2 herein.

As explained in more detail hereinafter, the Kingston process is not suitable for use with unpurified taxane mixtures. Osmium tetroxide catalyzed oxidation of cephalomannine is not amenable to impure extracts from biomass that contain taxol because of the strict reaction conditions required (purity of substrates, anhydrous reagents and solvents, etc.) for good transformation. The use of osmium tetroxide in the bulk manufacture of a pharmaceutical is also undesirable due to its severe toxicity.

There has not heretofore been provided a process for the simple, safe and effective oxidation of cephalomannine in the presence of taxol, nor has there been provided a process for the effective oxidation of cephalomannine in impure mixtures.

Also, there has not heretofore been provided a general, selective, and comprehensive process for oxidation of the olefin functional groups of taxanes to produce oxidized taxane compounds.

SUMMARY OF THE PRESENT INVENTION

In accordance with the present invention there is provided a process for chemically modifying cephalomannine and related compounds in the presence of taxol and other taxanes. The process of the invention can be performed in a manner such that no significant loss of taxol results.

The process of the invention is effective when treating pure mixtures of taxol, cephalomannine and other taxanes or when treating extracts of biomass containing very small amounts of these compounds in addition to other materials.

In the process of the invention, cephalomannine and other related compounds are chemically modified in the presence of taxol and other taxanes by treating the mixture of these compounds with ozone. The ozone reacts with cephalomannine and related compounds to produce several oxidized compounds, leaving essentially all of the taxol unchanged.

As used herein, the term "related compounds" includes taxanes with easily oxidizable olefin functional groups, e.g., an olefin group unsubstituted on one end.

The ozonolysis process for selective oxidation of cephalomannine and related taxanes in the presence of taxol and other taxanes is simple to perform, requiring only the solution of material (whatever the purity of taxol, cephalomannine and other taxanes) and an ozone generator capable of producing 1-10% ozone in an oxygen or air stream. The ozone is bubbled through the liquid mixture for the time required and the mixture is then purged with an inert gas. The material is then characterized and may be carried on to further purification.

In other words, after oxidation of the cephalomannine and related compounds, the conventional procedures for separation of taxol are faster and more easily performed. Consequently, the separation of taxol becomes more economical.

Figure 6:
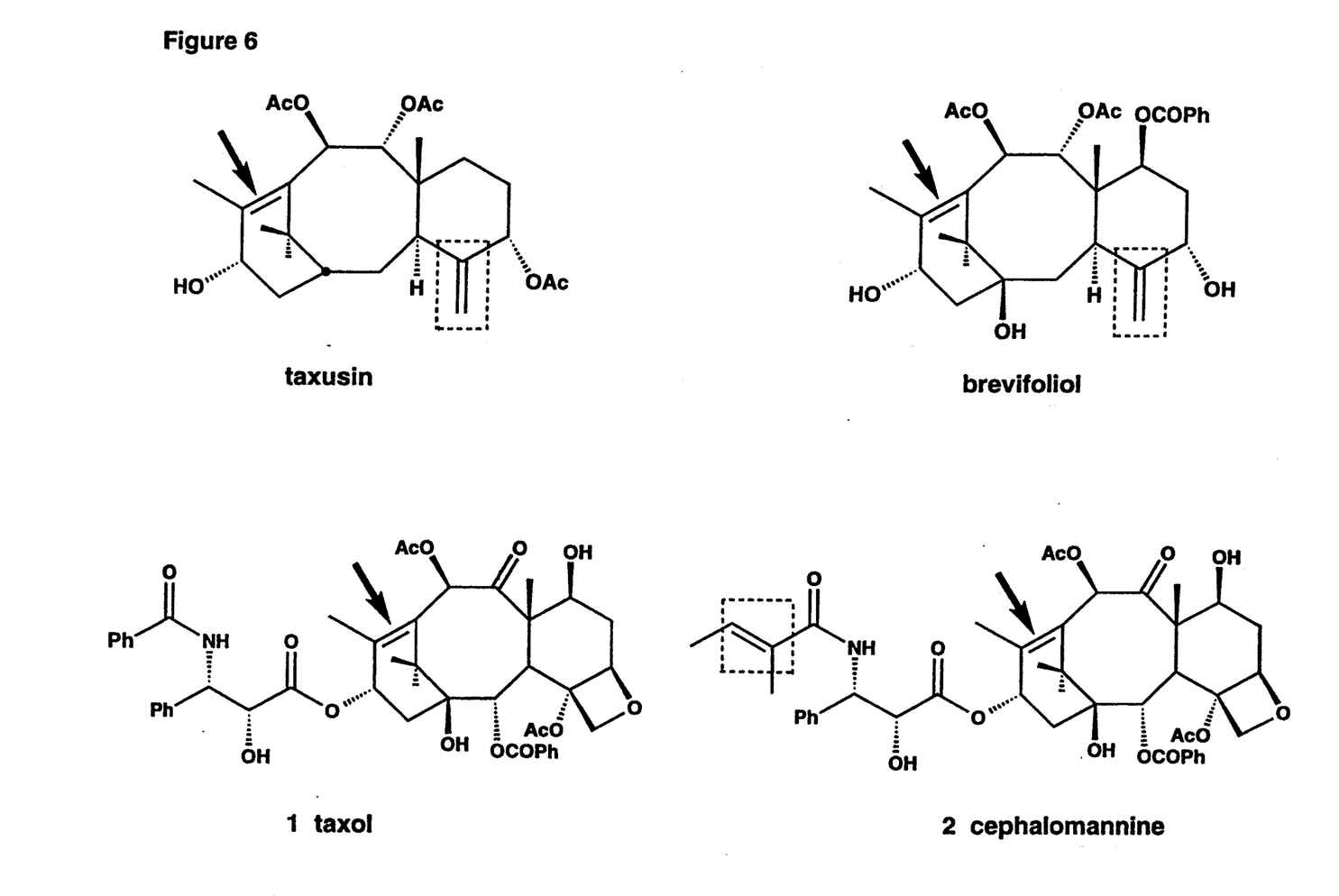
FIG. 6 shows the functional group selectivity of ozone with different taxanes.

The ozonolysis process for selective oxidation of cephalomannine and related compounds in the presence of taxol and other taxanes involves extensive oxidation of the olefin functional groups outlined by dotted lines in FIG. 6. The tetrasubstituted olefin (indicated by the arrow) in each of the structures in FIG. 6 is much less reactive than are the other olefins. Under proper conditions the tetrasubstituted olefin is essentially unchanged during the present oxidation process. The high selectivity of the ozone oxidation process for the outlined olefins is unexpected.

The ozonolysis process for selective oxidation of cephalomannine and related compounds in the presence of taxol and other taxanes is also efficient. For very pure mixtures of cephalomannine and taxol, between, but not limited to, 1 to 10 equivalents at room temperature of ozone are required for complete oxidation of the cephalomannine which does not result in significant loss of any of the taxol. For impure mixtures of taxol, cephalomannine, and other compounds the length of ozone treatment is dependent upon the concentration of impurities that react with ozone.

The ozonolysis process described herein is also mild. The window of treatment time for complete oxidation of cephalomannine and related compounds with no significant loss of taxol to oxidation can be carefully maintained. Once again, the length of ozone treatment depends upon the concentration of impurities.

The ozonolysis process of this invention does not depend upon the ratio of cephalomannine and related compounds to taxol and other taxanes. For example, the ratio of cephalomannine to taxol in the crude extracts of taxus brevifolia, as determined by High Pressure Liquid Chromatography—HPLC (with the UV detector set at 227 nm), is approximately 0.2. Other types of biomass have variable ratios of taxol and cephalomannine. The process of the invention has been effective for mixtures of the two compounds at or below the ratio of the crude extract of taxus brevifolia bark, and at ratios up to 7.35 (cephalomannine/taxol).

The ozonolysis process of this invention exhibits many advantages for purification purposes over oxidation methods employing other chemical oxidants (e.g., hydrogen peroxide, perchloric acid, sodium periodate, potassium permanganate, sodium hypochlorite, osmium tetroxide and peracetic acid). Oxidation using ozone is more rapid, more selective for cephalomannine in the presence of taxol, more complete for reasonable reaction times, and less toxic than the other listed oxidants in the process of this invention. In addition, ozone oxidation is more amenable to treatment of very crude mixtures of taxol and other taxanes and cephalomannine and related compounds than are other oxidants. Also, very important in the commercial purification of taxol is the fact that ozone can be introduced at an early point in the purification, whereas this is not practical when using osmium tetroxide.

In regards to purification, the use of ozone as an oxidant provides the same overall selectivity as is exhibited by the use of osmium tetroxide, while avoiding the toxicity problems.

In regards to providing a mild, selective, comprehensive route to oxidized taxanes, the use of ozone as an oxidant is superior to all of the oxidants listed above.

Other advantages of the process of the invention will be apparent from the following detailed description.

BRIEF DESCRIPTION OF THE DRAWINGS

The method is described in more detail hereinafter with reference to the accompanying schemes.

DETAILED DESCRIPTION OF THE INVENTION

The present invention relates to the high yield selective process for oxidation of cephalomannine in the presence of taxol in unpurified, partially purified, and purified mixtures. The oxidative process of this invention utilizes ozone to selectively transform taxanes similar to taxol but it does not significantly destroy the taxol. The selective oxidation of other taxanes, particularly cephalomannine, simplifies the isolation and purification of taxol.

The Kingston paper referred to above reported that their process was run on purified and partially purified taxane mixtures that contained cephalomannine and taxol (see FIG. 2). The partially purified mixture referred to was calculated to be 80% by weight for the taxol and cephalomannine. No reference was made to the usefulness of their process for mixtures below the 80% by weight level. Therefore, the Kingston process has not been evaluated for efficacy with a starting material that is very impure, for example, mixtures that contains less than 1% taxol by weight and less than 1% cephalomannine by weight. The Kingston process, and the process of the present invention are summarized in FIG. 2 and FIG. 3, respectively.

The Kingston process was repeated using purified cephalomannine (90% cephalomannine by weight, no taxol) to confirm the usefulness of their process for purified mixtures of taxanes. The experiment was run on 214 mg of cephalomannine using Kingston's reported method. The isolated product, 114 mg of cephalomannine-diol (57% yield), was characterized by spectroscopic methods and the data matched well with Kingston's reported data. The Kingston process was then performed on a dried, unpurified 505 mg sample of taxanes that contained 0.21% taxol by weight and 0.058% cephalomannine by weight (as determined by HPLC). The reaction was run in pyridine, the solvent used in the Kingston process. Several portions of excess osmium tetroxide were required to fully oxidize the cephalomannine in the crude mixture. A total of approximately 2000 molar equivalents of osmium tetroxide relative to cephalomannine were added. The reaction required eight days and the resulting crude mixture was very thick and difficult to manipulate. No further separation of the oxidized cephalomannine and taxol was attempted due to the very difficult manipulation of the mixture.

The numerous negative features of the Kingston stoichiometric process for selective oxidation of cephalomannine in the presence of taxol when applied to very impure mixtures include: the very long reaction time required for complete oxidation of cephalomannine; the very high ratio of osmium tetroxide to cephalomannine required for complete oxidation (the process is not economical—the osmium tetroxide reagent is very expensive—$76/gram from one common commercial supplier); the extremely careful handling required for the toxic osmium tetroxide reagent and the waste associated with the process; and the difficulties associated with manipulation of very thick reaction mixtures due to the high concentration of toxic transition metal and transition metal salts in the mixture.

The Kingston paper also describes a catalytic process for the oxidation of cephalomannine in the presence of taxol. The catalytic process is provided by Kingston as a method to reduce the cost and toxicity problems associated with osmium tetroxide. The catalytic process was repeated using purified cephalomannine (90% cephalomannine by weight) to confirm the usefulness of this process for purified mixtures of taxanes. The experiment was performed at 0° C. on 6.5 mg of cephalomannine (90% by wt.) in acetone solvent to yield a mixture that contained the expected diol as determined by HPLC comparison with a standard of the diol that was prepared via the stoichiometric route. The Kingston process was then performed on a dried 1.4 g sample of impure taxanes that contained 0.21% taxol by weight and 0.058% cephalomannine by weight (as determined by HPLC). The taxane sample was not very soluble in the acetone solvent system, even with sonication. Addition of the catalyst system followed by stirring resulted in no decrease in the amount of cephalomannine in the mixture even after several days reaction time. Therefore, the negative feature of the process for catalytic osmium tetroxide oxidation of cephalomannine in the presence of taxol as described by Kingston, is that it does not work for very impure mixtures of taxanes. In summary, the Kingston processes employing osmium tetroxide for the selective oxidation of cephalomannine in the presence of taxol are not suitable for very impure mixtures of taxanes.

Figure 3:
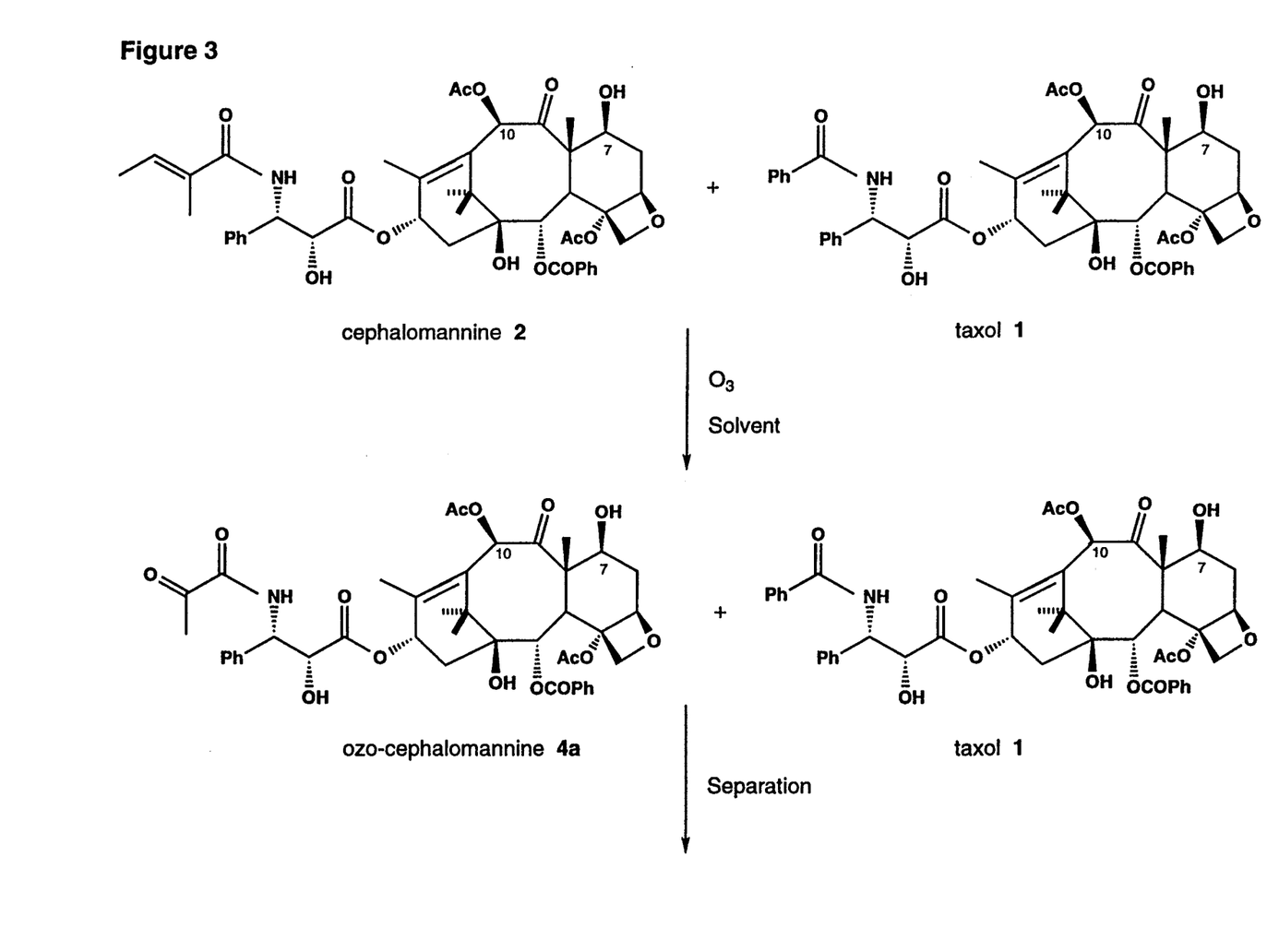
FIG. 3 shows the overall selectivity of ozone on mixtures of taxol and cephalomannine.

The preferred embodiment of the present invention includes contacting a mixture of taxanes containing cephalomannine and taxol with ozone in stoichiometric quantities (see FIG. 3). In the preferred process ozone is employed due to its greater efficiency, lower cost, and lower toxicity as compared to the use of osmium tetroxide. The present invention is effective for the selective oxidation of susceptible taxanes as very pure single compounds or in very pure mixtures. Samples of pure cephalomannine or a 50:50 mixture of pure taxol and pure cephalomannine, work well, for example. In addition, the present invention is also effective for the selective oxidation of susceptible taxanes in very crude mixtures of taxanes. The crude extracts of biomass work well, for example. The Kingston process has only been demonstrated as useful for purified or partially purified mixtures of taxanes at greater than or equal to 80% purity by weight. It has been demonstrated herein that the Kingston process is not useful for very impure mixtures of taxanes. The usefulness of the present invention for the selective oxidation of samples of susceptible taxanes at a wide range of purities provides a significantly improved commercial process when compared to the process developed by Kingston.

Figure 4:
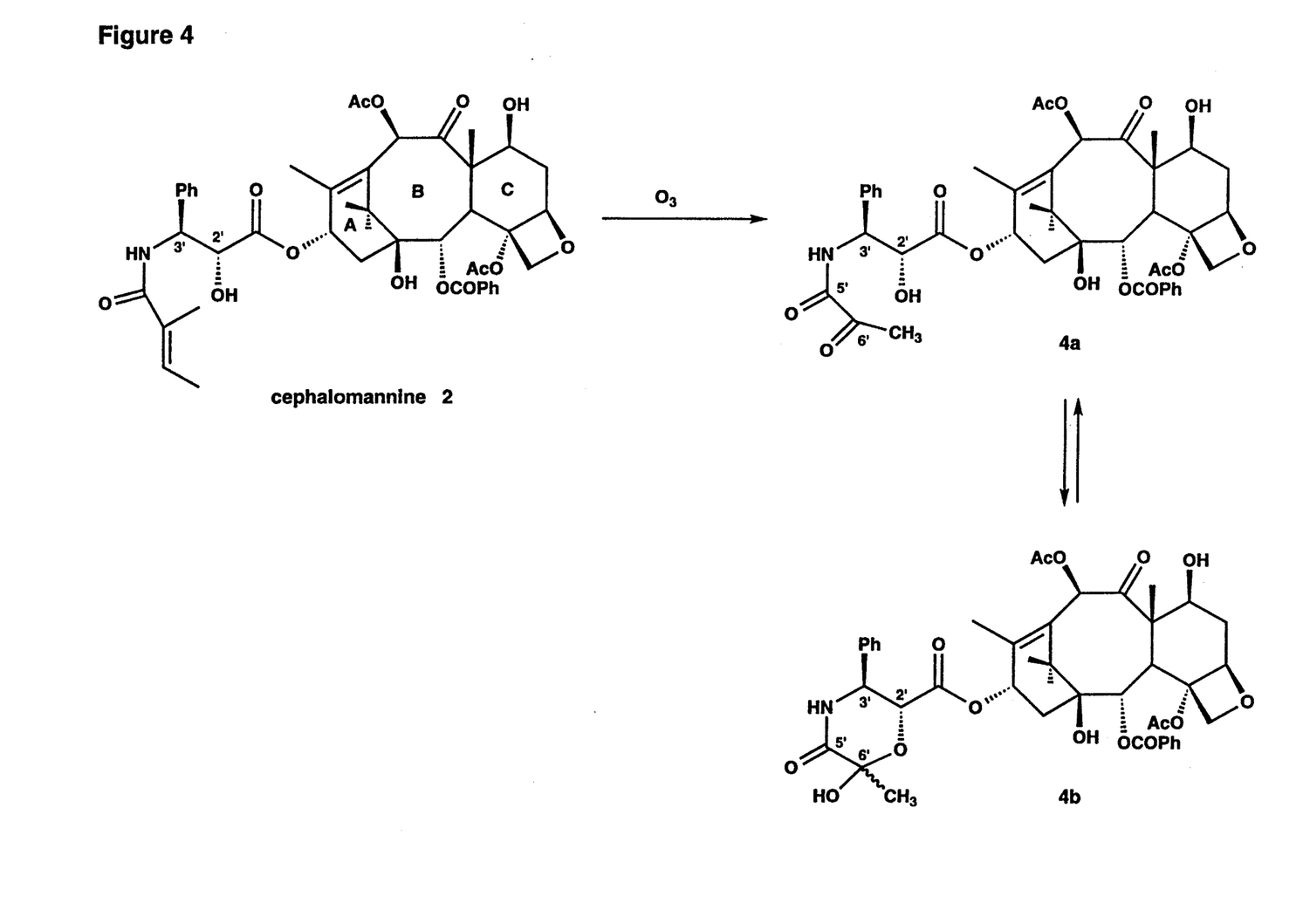
FIG. 4 shows the reaction of cephalomannine with ozone.
Figure 5:
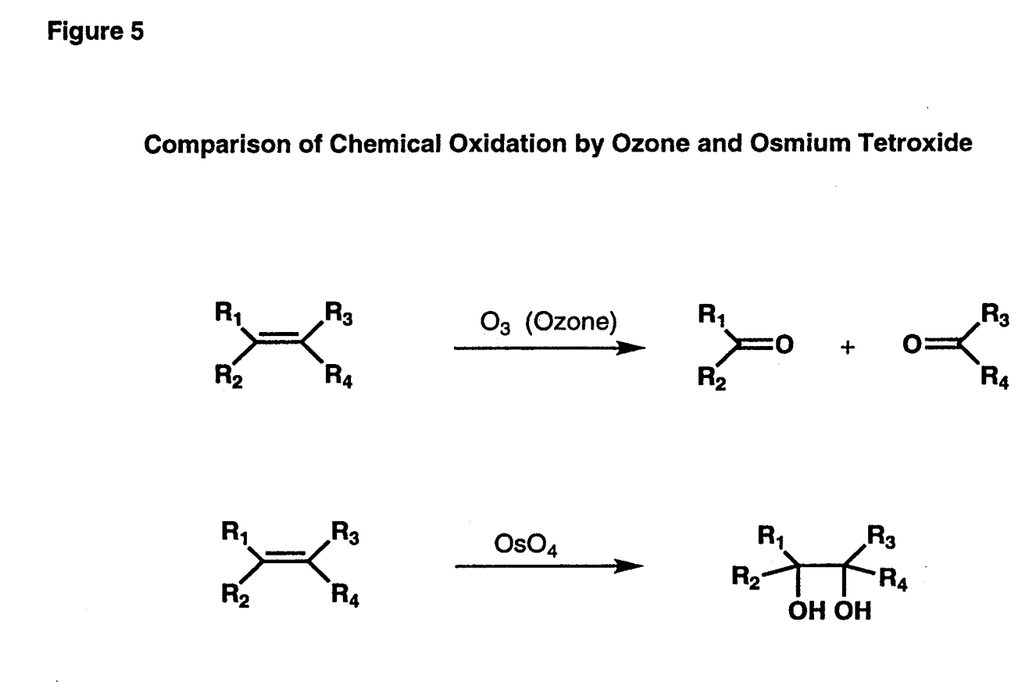
FIG. 5 shows a comparison of chemical oxidation by ozone and osmium tetroxide.

The process of oxidation of purified cephalomannine by treatment with ozone was performed on cephalomannine that was 90% by weight. Treatment of a solution of cephalomannine (2.70 g) in methylene chloride with 1.2 equivalents of ozone results in a quantitative yield of the compound mixture 4a and 4b. The predominant form in non-alcoholic solvents is 4a (see FIG. 4). The compound mixture 4a/4b has been characterized fully by spectroscopy and other methods. FIG. 5 highlights the difference in products formed with the present invention versus the Kingston process. Ozone results in the oxidative cleavage of the olefin bond, osmium tetroxide results in the dihydroxylation of the olefin bond. No olefin bond cleavage occurs with the osmium tetroxide process. Structures 3 and 4a/4b show the different products formed by the two different processes. Structures 4a/4b have two less carbons due to the oxidative cleavage.

The process of oxidation of unpurified cephalomannine by treatment with ozone was also performed on a dried, unpurified 1.24 g sample of taxanes that contained 0.21% taxol by weight and 0.058% cephalomannine by weight (as determined by HPLC). The sample was dissolved in methanol and cooled to 0° C. Ozone was then bubbled through the solution. Small aliquots were removed for analysis by HPLC after addition of every 50 or 100 equivalents of ozone. The HPLC method indicated the cephalomannine was completely oxidized by treatment with between 350 to 400 equivalents of ozone. The HPLC method also showed no degradation of the taxol. The mixture was taken on to further purification and the oxidized cephalomannine was separated from the taxol by chromatography or other methods.

For partially purified mixtures of cephalomannine and taxol containing ratios of cephalomannine/taxol of 0.05 to 7.35 (purity of taxol or cephalomannine is between 1 and 5% by weight) the process is similar to that described above. The mixture of cephalomannine and taxol (a dry powder which is green, yellow, red, or white in color, with purities ranging from 1% taxol to 99.5% taxol) is dissolved in an organic solvent (for example, methyl alcohol or methylene chloride), after which ozone is bubbled through the solution until the cephalomannine is completely oxidized. The reaction can be monitored be HPLC analysis as described in the Examples section. After the oxidation is finished, the reaction mixture is purged with nitrogen gas to remove excess ozone. In all cases the cephalomannine and related compounds are oxidized with high recovery of taxol. The taxol is then purified from the resulting mixture using a variety of methods, for example, chromatography or crystallization. The transformation of cephalomannine to a more polar compound, ozo-cephalomannine, 4a/4b eases the normally difficult separation of taxol and cephalomannine.

The number of molar equivalents of ozone added is dependent upon the purity of the mixture (wt % of taxol and cephalomannine), and the concentration of cephalomannine and other compounds that react with ozone. Generally, less pure mixtures of taxanes require more molar equivalents (relative to cephalomannine) of ozone to completely oxidize the cephalomannine, than pure mixtures of taxanes. The less pure mixtures of taxanes contain several compounds that compete with the cephalomannine for the available ozone introduced into the mixture. See, for example, FIG. 6, showing taxusin and brevifoliol, which compounds have olefin functional groups (outlined with the dotted line) that react with ozone.

For the more pure mixtures of cephalomannine and taxol (i.e., greater than 5% by weight of either cephalomannine or taxol) solvent may be added to the solids to make solutions. The solutions are then treated with ozone for the appropriate time by monitoring the progress of the reaction with HPLC for the disappearance of the targeted compounds.

Solvents that may be used for this process include saturated and unsaturated hydrocarbons, halogenated solvents, alcohols, ethers, aldehydes, ketones, amines, organic acids, organic acid derivatives, water, and mixtures thereof. Methylene chloride, chloroform, or methyl alcohol, or mixtures thereof are the preferred solvents for this process.

The oxidation process is effective over a wide range of temperatures. Temperatures that were investigated include but are not limited to −100° C. to 50° C.

The ozone is available, for example, from an ozone generator capable of producing at least 8 grams of ozone an hour (0.42 pounds/day) at no less than 1% weight concentration in clean, dry air (−600° F. dewpoint) when operated with 115 volt, 60 Hertz current and 8 psig pressure; or at least 16 grams of ozone an hour (0.85 pounds/day) at no less than 2% weight concentration in pure, clean, dry oxygen (−600° F. dewpoint) when operated with 115 volt, 60 Hertz current and 8 psig pressure. The concentration of ozone in the oxygen stream can be determined by a variety of methods. Titrametric analysis of an acidic potassium iodine solution after specific treatment times with ozone is a preferred method. The use of sudan red 7B (a dye) has been reported for following ozonolysis reactions. In addition, calibrated ozone meters are available from certain manufacturers. The ozone may also be delivered to the reaction mixture as a solution of ozone in solvent.

The use of ozone in an oxidation process with a fairly sensitive natural product such as taxol would not be expected to leave the taxol unaffected. This is especially true considering that taxol, cephalomannine, taxusin, and brevifoliol all have an olefin functional group in the A ring (see the arrows in FIG. 6) which might be expected to react with ozone. In addition, taxol and other taxanes contain many functional groups that are susceptible to oxidation, such as tertiary hydrogen atoms, aryl rings, and ethers. The high yield and selective ozone oxidation of the tiglate tail portion of cephalomannine in unpurified, partially purified, and purified mixtures of taxanes, under a variety of conditions is not obvious to one skilled in the art.

In the process of this invention, taxol is not significantly degraded by ozone, and the selective oxidation of cephalomannine and related taxanes in the presence of taxol and related taxanes using ozone relies upon the functional group differences between cephalomannine along with related compounds, and taxol. It is important to note, however, that taxol will degrade to several unidentified compounds by improper exposure to a large excess of ozone or from improper exposure to a slight excess for an extended period. The degradation of taxol by ozone can be avoided if the reaction is monitored carefully by TLC or HPLC. The following examples provide procedures for carrying out the selective ozone oxidation of samples containing taxol and cephalomannine without significant degradation of taxol.

The positive features of the present invention when compared to the Kingston process include: very fast reaction times; easily controlled addition of oxidizing reagent; a process that is flexible enough to efficiently oxidize cephalomannine and related compounds in mixtures at a wide range of purities (purity levels tested include mixtures containing cephalomannine and taxol at less than 0.3% by weight to mixtures that contain cephalomannine and taxol at greater than 95% by weight in a 1:1 mixture); inexpensive and easily handled reagents and reaction mixtures; and very little toxic waste associated with the reaction.

EXAMPLES

The following examples provide specific processes for the selective oxidation of cephalomannine and other susceptible taxanes in unpurified, partially purified or purified samples of taxanes. These selective oxidations work equally well for samples that contain ozone susceptible taxanes with or without taxol. All scientific and technical terms have the meanings as understood by one with ordinary skill in the art. The term "biomass" as used herein includes taxus species and cell culture of taxus species. The impure mixtures, i.e., crude biomass extracts can be obtained, for example, by methods described in a recent publication (Rao, Koppaka V., "Method for the Isolation and Purification of Taxane Derivatives" International Publication Number, WO 92/07842, May 14, 1992), incorporated herein by reference.

All solvents and reagents employed were used as received from the manufacturer except pyridine which was distilled prior to use. Reactions were monitored by thin-layer chromatography ("TLC") using 0.20 min. E. M. Industries Silica Gel 60 (aluminum support) silica gel plates. Reactions were also monitored by high pressure liquid chromatography ("HPLC"). Aliquots of crude reaction mixtures for HPLC analysis were removed from the reaction vessel with micro-pipette and diluted to 200 μl in an HPLC sample vial (with insert). The HPLC system consists of a model L-6200 pump, Model AS-4000 or L-3000 UV/VIS/DAD detector (Hitachi Instruments, Inc.). The system was equipped with an NEC 286 computer with 40M hard drive and Lab Manager HPLC software (Hitachi Instruments, Inc.). HPLC columns used included a 4.6 mm.×250 mm. Phenyl column, packed with 5 μm diphenyl material (Supelco, Inc.), a 4.6 mm×250 mm 5 μm, 60 angstrom Pentafluorophenyl (PFP) column (ES Industries); and a 4.6 mm.×250 mm. phenyl guard column (Jones Chromatography). The ozone generator used was a Polymetrics Laboratory Ozonator T-816. The ozone delivery concentration was 0.0046 mmole/second at settings of 100 volts, 60 Hz current, 3.0 psig pressure and a flow rate of 2 SLMP. The ozone flow was calibrated using the method described by the manufacturer. Silica gel for flash chromatography (230 to 400 mesh) was supplied by Scientific Products. A Bruker WP-270 and ACE-300, Varian Gemini 400, and a JEOL FX90Q Spectrometer were employed for $^1H$ and $^{13}C$ NMR spectra with chemical shifts reported in ppm. relative to tetramethylsilane using residual non-deuterated NMR solvent for reference. Yields refer to chromatographically pure compounds and are not optimized. Purity of products were judged to be >90% on the basis of spectrophotometric homogeneity unless otherwise stated. Chrom purity as used herein refers to the HPLC normalized peak area percentage at 227 nm for a given component. Mass spectra were measured at M-Scan Inc. using a VG Analytical 2-SE high field mass spectrometer. Spectroscopic analyses were determined using an Analect Diamond-20 FTIR with an XAD-Phs microscope. The instrument was equipped with an ACR Advanced Logic Research 486 computer with 200M hard drive and an Analect FX80 software package.

EXAMPLE I (PRIOR ART)

Procedure for oxidation of purified cephalomannine with $OsO_4$ (stoichiometric reaction). $OsO_4$ in pyridine (0.020M, 24. 5 ml, 2.1 equivalents) was added to a solution of cephalomannine (192 mg, 0.23 mmol) in dry pyridine (12.88 ml, 0.02M), and mixed for 19 hours at room temperature. The reaction was then quenched with 10% $NaHSO_3$ (43 ml) and mixed for 2.5 hours. The mixture was acidified with 3N HCl to pH 1 (paper) and extracted 3 times with EtOAc. The organic layer was washed twice with brine, dried over $Na_2SO_4$, and evaporated. The light green residue was chromatographed on silica gel (gradient EtOAc/hexane) giving 114 mg (57% yield) of a white solid ($R_f$=0.41, 10:90 MeOH/$CH_2Cl_2$). The spectrometric analyses match with Kingston's reported values ("Modified Taxols, 7. A Method For The Separation Of Taxol And Cephalomannine", Journal of Natural Products, 55, 259–261, (1992)).

EXAMPLE II (PRIOR ART)

Procedure for oxidation of purified cephalomannine with $OsO_4$ (catalytic reaction). To 5.9 mg (0. 007 mmol) of cephalomannine dissolved in acetone was added tetraethylammonium acetate (0.7 mg, 0.003 mmol, 0.43 equivalents). The mixture was cooled to 0° C. and t-butyl hydroperoxide (1.7 μl, 2.54 equivalents of a 70% H$_2$O solution) and osmium tetroxide (2.5 μl, 0.029 equivalents of a 0.070M solution in t-butyl alcohol) were added. The mixture was stirred for one hour at 0° C. and then 1.5 hours at room temperature. A sample was analyzed by HPLC and the reaction appeared to be finished. The HPLC and TLC data indicate a very similar product mixture was formed by the catalytic method as by the stoichiometric method.

EXAMPLE III

Procedure for the oxidation of pure ceph with O$_3$.

Cephalomannine 3 (90% by weight, total weight: 2.702 g; cephalomannine: 2.432 g, 29.24 mmol) in CH$_2$Cl$_2$ (65 ml, 0.45M) at $-60°-$$-75°$ C. was treated with ozone (39.744 mmol, 0.0046 mmol/s, 1.4 equivalents) for 184 minutes. The solution was then purged with argon at room temperature for 5 minutes following evaporation. Analysis by HPLC indicated the reaction was complete, and NMR showed the equilibrium mixture of 4a and 4b. Resonances for the major compound are listed. $^1$H NMR (90 MHz, CDCl$_3$) 1.11 (s,3H) 1.21 (s,3H) 1.29–1.58 (m, 2H), 1.64 (s, 3H), 1.78 (s, 3H), 1.89–2.16 (m, 3H), 2.20 (s, 3H), 2.31 (s, 3H), 2.24 (s, 3H), 2.40–2.72 (m, 1H), 3.75 (d, J=6.8 Hz, 2H), 3.98–4.47 (m, 3H), 4.64 (m, 1H), 4.89 (d, J=8.5 Hz, 1H), 5.13–5.68 (m, 2H), 5.98–6.20 (m, 1H), 6.25 (s, 1H), 7.27–7.73 (m, 8H), 7.85 (d, J=9.4 Hz, 1H), 8.07 (d, J=7.7 Hz, 2H). $^{13}$C NMR (12 MHz, CDCl$_3$) 9.54, 14.65, 20.76, 21.65, 22.51, 24.37, 26.79, 35.62, 35.62, 43.12, 45.72, 55.00, 58.48, 72.04, 72.04, 73.31, 74.96, 75.58, 76.44, 79.00, 81.16, 84.32, 126.97, 126.97, 128.60, 128.60, 128.60, 128.89, 128.89, 129.16, 130.11, 130.11, 133.24, 133.65, 137.14, 141.68, 159.70, 166.88, 170.30, 171.07, 171.93, 195.94, 203.55. The diagnostic signals in the $^{13}$C-NMR spectrum for the minor isomer in CDCl$_3$ (carbon 6' of the two diastereomers of 4b) are 102.52 and 105.35 ppm. The diagnostic signals in CD$_3$OD of 4ab, including possible solvent addition (CD$_3$OD) to both 4a and 4b are 97.9 and 197.2 ppm. FTIR (neat, cm$^{-1}$) 981.6 (m), 1025.9 (m), 1070.3 (m), 1108.9 (m), 1178.3 (m), 1241.9 (s), 1373.1 (m), 1724.0 (s), 2900.4 (w), 2940.9 (w), 3064.3 (w), 3413.4 (m), 3490.5 (m). The melting point of an analytically pure sample (chrom purity>97%) was 162°–167° C. Mass Spectrum (FAB, glycerol/thioglycerol matrix) m/z 821 (M+1)+.

EXAMPLE IV

Oxidation of impure cephalomannine/taxol with OsO$_4$ (stoichiometric). Dried natural product extract (505.3 mg) containing cephalomannine (0.3 mg, 0.058% by weight) was dissolved in dry pyridine (1.3 ml). To the solution was added in portions OsO$_4$ in pyridine (0.077M) over a seven day period at room temperature until no cephalomannine remained as shown by HPLC. It took between 1,176 and 1,990 equivalents of OsO$_4$ (5.345 ml and 9.045 ml) to completely oxidize the available cephalomannine.

EXAMPLE V

Oxidation of impure cephalomannine/taxol with OsO$_4$ (catalytic).

A suspension of dried, ground biomass extract (1.40 g) containing 0.81 mg cephalomannine (0.058% by weight) was prepared in acetone (1.5 ml originally), and 3×0.5 ml portions were added to facilitate mixing. The initially liquid/granular mixture turned into a liquid/gummy tar within ten minutes. The liquid was sampled for HPLC analysis. Tetraethylammonium acetate (0.08 mg, 0.32 equivalents) was added and the mixture was cooled to 0° C. To this mixture was added t-butyl hydroperoxide (0.3 μl, 2.28 equivalents of a 70% H$_2$O solution) followed by addition of osmium tetroxide (0.3 μl, 0.025 equivalents of a 0.79M solution). The mixture was stirred for 1.25 hours at 0° C., and then 2 hours at room temperature. At this point, no oxidation of cephalomannine was observed when a small aliquot was removed from the mixture and analyzed by HPLC. Additional aliquots were removed after 17.75 and 25.75 hours of total reaction time. The HPLC analysis of these samples indicated no decrease in the amount of cephalomannine or increase in the amount of expected diol.

EXAMPLE VI

Oxidation of impure cephalomannine/taxol with O$_3$. Dried natural product extract (1.24 g) containing cephalomannine (0.7 mg, 0.058% by weight) was dissolved in MeOH (5 ml) and cooled to 0° C. O$_3$ was then bubbled through the solution while taking samples at various times for HPLC analysis. These aliquots (~3 μl) were immediately diluted in THF/Me$_2$S in order to reduce the remaining O$_3$ prior to analysis. The data shows 350 to 400 eq. O$_3$ was necessary to fully oxidize the cephalomannine.

EXAMPLE VII

Procedure for the oxidation of partially purified ceph/tax with O$_3$. A mixed sample of taxol (91.1 mg, 0.11 mmole) and cephalomannine (92.2 mg, 0.11 mmole) was prepared. The mixture was dissolved in dry methylene chloride and a small aliquot was removed for analysis of the starting mixture. Ozone was bubbled through the cooled (0° C.) solution for 134 seconds followed by an argon purge. The ozone delivered to the mixture corresponds with 5.6 molar equivalents relative to cephalomannine (the ozone generator was calibrated as delivering 0.0046 mmole/second at specific settings prior to the reaction). The crude mixture was sampled for HPLC analysis and the solution was evaporated. The residue was chromatographed (SiOn, 3% n-BuOH/CH$_2$Cl$_2$) to yield 50 mg of taxol (55% recovery) at chrom purity>93%. These fractions contained no cephalomannine or oxidized cephalomannine. This procedure was not optimized. The ratio of cephalomannine/taxol used for this experiment is five times the ratio normally seen with biomass from *Taxus brevifolia*. Consequently, the recovery and purities obtained using the process presented herein and starting with the normal ratio of cephalomannine/taxol (0.18 to 0.21) would be much better. The process greatly improves the purification of taxol from cephalomannine.

Other variants are possible without departing from the scope of this invention.

What is claimed is:

1. A process for oxidizing cephalomannine in the presence of taxol in a solution comprising contacting said solution with ozone.

2. A process in accordance with claim 1, wherein said solution comprises a solvent selected from the group consisting of hydrocarbons, halogenated solvents, alcohols, ethers, aldehydes, ketones, amines, organic acids, organic acid derivatives, water, and mixtures thereof.

3. A process in accordance with claim 1, wherein ozone is bubbled through said solution.

4. A process in accordance with claim 1, wherein the ozone is contained in a liquid which is added to said solution.

5. A process in accordance with claim 1, further comprising the step of monitoring said solution to determine extent of oxidation of oxidizable cephalomannine; wherein said monitoring comprises use of HPLC; and wherein ozone is bubbled through said solution until the absence of cephalomannine is ascertained.

* * * * *